US012773223B2

(12) United States Patent
Reich

(10) Patent No.: US 12,773,223 B2
(45) Date of Patent: Oct. 27, 2026

(54) ORTHOPEDIC REAMING TOOL

(71) Applicant: Zimmer, Inc., Warsaw, IN (US)

(72) Inventor: Aiden Sawyer Reich, Outremont (CA)

(73) Assignee: Zimmer, Inc., Warsaw, IN (US)

( * ) Notice: Subject to any disclaimer, the term of this patent is extended or adjusted under 35 U.S.C. 154(b) by 153 days.

(21) Appl. No.: 18/443,622

(22) Filed: Feb. 16, 2024

(65) Prior Publication Data

US 2024/0341777 A1 Oct. 17, 2024

Related U.S. Application Data

(60) Provisional application No. 63/458,773, filed on Apr. 12, 2023.

(51) Int. Cl.
*A61B 17/16* (2006.01)
*A61B 17/00* (2006.01)
*A61B 17/56* (2006.01)

(52) U.S. Cl.
CPC *A61B 17/1684* (2013.01); *A61B 2017/00477* (2013.01); *A61B 2017/564* (2013.01)

(58) Field of Classification Search
CPC .................................................. A61B 17/1684
See application file for complete search history.

(56) References Cited

U.S. PATENT DOCUMENTS

| | | | | |
|---|---|---|---|---|
| 5,489,310 A * | 2/1996 | Mikhail | A61F 2/4081 | 623/19.11 |
| 9,408,613 B2 * | 8/2016 | Kehres | A61B 17/1684 | |
| 9,603,607 B2 * | 3/2017 | Papenfuss | A61B 17/1617 | |
| 9,763,679 B2 * | 9/2017 | Lappin | A61B 17/1778 | |
| 9,814,471 B2 * | 11/2017 | Goldberg | A61B 17/1631 | |
| 10,548,617 B1 * | 2/2020 | Olson | A61B 17/17 | |
| 10,687,831 B2 | 6/2020 | Kovacs et al. | | |
| 10,945,862 B2 | 3/2021 | Roby et al. | | |
| 11,234,717 B2 * | 2/2022 | Cardon | A61B 17/1659 | |
| 11,246,604 B2 * | 2/2022 | Rodriguez | A61B 17/1631 | |
| 2007/0142840 A1 * | 6/2007 | Goodwin | A61B 17/1684 | 606/81 |
| 2011/0028977 A1 * | 2/2011 | Rauscher | A61B 17/1684 | 606/80 |
| 2013/0138109 A1 * | 5/2013 | Long | A61B 17/1684 | 606/80 |
| 2015/0119891 A1 * | 4/2015 | Goldberg | A61B 17/1778 | 606/80 |
| 2015/0257769 A1 * | 9/2015 | Papenfuss | A61B 17/1668 | 606/80 |
| 2015/0265288 A1 * | 9/2015 | Guederian | A61B 17/1684 | 606/80 |
| 2017/0049461 A1 * | 2/2017 | Papenfuss | A61B 17/1668 | |
| 2017/0303936 A1 * | 10/2017 | Weekes | F16D 1/02 | |
| 2018/0008293 A1 * | 1/2018 | Kovacs | A61B 17/1659 | |
| 2018/0280037 A1 * | 10/2018 | Dassonville | A61B 17/1633 | |
| 2021/0196288 A1 * | 7/2021 | Hodorek | A61B 17/1684 | |

* cited by examiner

*Primary Examiner* — Zade Coley
(74) *Attorney, Agent, or Firm* — SCHWEGMAN LUNDBERG & WOESSNER, P.A.

(57) ABSTRACT

A bone cutting instrument may include a first component having one or more cutting features configured to remove a fossa of a scapula and a second component having one or more cutting features configured to remove at least a vault of the scapula. The second component can be selectively moveable relative to the first component to remove at least a portion of the vault and is configured to engage the first component to drive the first component for removing the fossa.

8 Claims, 5 Drawing Sheets

ORTHOPEDIC REAMING TOOL

CLAIM OF PRIORITY

This application claims the benefit of U.S. Provisional Patent Application Ser. No. 63/458,773, filed on Apr. 12, 2023, the benefit of priority of which is claimed hereby, and which is incorporated by reference herein in its entirety.

FIELD OF THE DISCLOSURE

The present disclosure relates to orthopedic apparatuses such as a reaming tool for use during an arthroplasty procedure.

BACKGROUND

In the human body, tissue can require repair. Such tissue includes bone, muscles, tendons, ligaments and cartilage. Forceful twisting, trauma or rotation of a joint can tear or otherwise damage tissue. Disease can also necessitate replacement of bone(s) of the joint with one or more prosthetic components. Thus, a surgical repair of the tissue may be required in various circumstances.

Such replacement can require reaming or other cutting and preparation of bone to receive a prosthesis. While cutting instruments are known and are generally effective for their intended purposes, improved cutting instruments for facilitating cutting/preparation of the bone are still desirable.

In a healthy shoulder, the proximal humerus is generally ball-shaped, and articulates within a socket, called the glenoid, formed by the scapula to form the shoulder joint. Conventional implant systems for the total replacement of the shoulder joint due to disease or trauma, i.e., a total shoulder arthroplasty, generally replicate the natural anatomy of the shoulder, and typically include a humeral component having a stem which fits within the humeral canal, and an articulating head which articulates within the socket of a glenoid component implanted within the glenoid of the scapula.

Various types of shoulder implant systems are known including for conventional or reverse joint replacement, revision shoulder arthroplasty and a partial (hemi) shoulder arthroplasty.

SUMMARY

The present disclosure provides orthopedic cutting instruments having two or more components each with cutting features. Disclosed apparatus and methods can be used for various purposes including shoulder joint repair.

The present inventor has realized that certain aspects of joint replacement procedures such as reaming the glenoid during a shoulder replacement procedure can be overly complex, difficult and time consuming. These difficulties result from a size of the reamer including a length of vault reaming portion during approach, the reamer's approach orientation, and/or the patient's soft tissue and other surrounding instruments interfering with the approach of the reamer to the glenoid. As a result, surgeons must work to manipulate the reamer or surrounding instruments and/or soft tissue to achieve desired reaming of the glenoid. Such manipulation can increase the incision's work area. This may also result in an oblong reaming if the instrumentation (retractors) remain in contact with the reamer tool. Such manipulation can be undesirable as the process is time consuming and requires an undesirable amount of surgical effort. In some cases, the surgeon may be forced by one or more of the above factors to select a smaller instrument than would otherwise be desirable, and hence a smaller implant than would otherwise be desirable. In cases where a surgical robot is utilized and the approach angle is fixed, the surgeon may not be able to utilize the surgical robot and must revert to standard instrumentation.

The present inventor has developed a cutting instrument for performing both reaming of the vault and the fossa in a single step. This is in contrast to typical reaming tools that ream the vault in a separate step from the fossa. Additionally, the present inventor has recognized a cutting instrument for reaming that reduces an initial distal length of the vault reaming component during approach when locating of the cutting instrument on the glenoid. More particularly, the length of the vault is inverted during approach and when locating to have a proximal length of the vault reaming portion above the remainder of the cutting instrument. This makes the approach of the cutting instrument to the glenoid more manageable and less time consuming as surgical complexity and effort is reduced. More particularly, the present inventor recognizes that providing for the cutting instrument with a vault reaming component that is telescopically received or otherwise retracted relative to a fossa reaming component can allow the vault reaming component to be moveable (e.g., extendible and retractable) relative to the fossa reaming component. Retraction of the vault reaming component can reduce an initial length of the cutting instrument inserted into the shoulder joint and positioned adjacent the glenoid. This reduced length for the vault reaming component on the distal side of the cutting instrument when approaching the glenoid can allow the cutting instrument to be more easily manipulated into a desired position relative to the glenoid to perform reaming. A retractable and extendible vault reaming component can also allow a longer vault reaming length to be used than would otherwise be possible with a conventional glenoid shoulder reamer and can also allow a larger fossa size to be used in conjunction (or simultaneously) than would otherwise be possible.

The above discussion is intended to provide an overview of subject matter of the present patent application. It is not intended to provide an exclusive or exhaustive explanation of the invention. The description below is included to provide further information about the present patent application To better illustrate the apparatus and methods disclosed herein, a non-limiting list of examples and techniques is provided here:

In some aspects, the techniques described herein relate to an apparatus for removing bone during an orthopedic procedure, the apparatus can optionally include: a first component having one or more cutting features configured to remove a fossa of a scapula; and a second component having one or more cutting features configured to remove at least a vault of the scapula, wherein the second component is selectively moveable relative to the first component to remove at least a portion of the vault and is configured to engage the first component to drive the first component for removing the fossa.

In some aspects, the apparatus, further optionally including a retention assembly configured to couple the first component with the second component but allow the second component to be selectively moveable relative to the first component while the second component is in a retracted state relative to the first component.

In some aspects, the apparatus, wherein optionally the retention assembly includes: at least one bushing coupled to one or both of the first component and the second component; and a spring configured to bias the second component to the retracted state relative to the first component.

In some aspects, the apparatus, wherein optionally the at least one bushing is fit to at least the second component, and wherein the spring is coiled around the second component and engages that at least one bushing at a first end thereof In some aspects, the apparatus, further optionally including: a first plurality of engagement features positioned along the first component; and a second plurality of engagement features positioned along the second component, wherein rotation of the second component brings the second plurality of engagement features into contact with the first plurality of engagement features to engage the second component with the first component for removing the fossa and vault simultaneously.

In some aspects, the apparatus, further optionally including one or more ramps that pass the second plurality of engagement features to the first plurality of engagement features.

In some aspects, the apparatus, wherein optionally the one or more cutting features of the second component substantially align with the one or more cutting features of the first component when the second component is in a deployed state and engaged with the first component for removing the scapula.

In some aspects, the techniques described herein relate to an apparatus for removing part of a scapula during an orthopedic shoulder procedure, optionally including: a first component having one or more cutting features configured to remove a fossa of scapula; and a second component having one or more cutting features configured to remove at least a vault of the scapula, wherein the second component is selectively moveable relative to the first component between a retracted position and a deployed position, wherein the second component and the first component are coupled together for rotation when the second component is in the deployed position.

In some aspects, the apparatus, further optionally including a retention assembly configured to couple the first component with the second component, the retention assembly including: a first bushing coupled to the first component; a second bushing coupled to the second component; and a spring engaging the first bushing and the second bushing, wherein the spring is configured to bias the second component to the retracted position relative to the first component.

In some aspects, the apparatus, further optionally including: a first plurality of engagement features positioned along the first component; and a second plurality of engagement features positioned along the second component, wherein rotation of the second component brings the second plurality of engagement features into contact with the first plurality of engagement features to engage the second component with the first component for removing the fossa and vault simultaneously.

In some aspects, the apparatus, further optionally including one or more ramps that pass the second plurality of engagement features to the first plurality of engagement features.

In some aspects, the apparatus, wherein optionally the one or more cutting features of the second component substantially align with the one or more cutting features of the first component when the second component is in the deployed position and engaged with the first component for removing the scapula.

In some aspects, the techniques described herein relate to a method of cutting a bone during an orthopedic surgical procedure, the method optionally including: rotating and inserting at least a portion of a cutting instrument through a second cutting instrument to remove at least part of a vault of the scapula; engaging the cutting instrument with the second cutting instrument; and upon the engaging, rotating the cutting instrument and the second cutting instrument to remove a fossa of the scapula.

In some aspects, the method, wherein optionally the engaging the cutting instrument with the second cutting instrument is via a plurality of engagement protrusions.

In some aspects, the method, further optionally including passing at least some of the one or more engagement protrusions along ramps of the second cutting instrument.

In some aspects, the method, wherein optionally the cutting features of the cutting instrument and the second cutting instrument are aligned upon the engaging of the cutting instrument with the second cutting instrument.

In some aspects, the method, wherein optionally rotating and inserting the at least the portion of the cutting instrument includes compressing a spring coupled between the cutting instrument and the second cutting instrument.

In some aspects, the method, further optionally including isolating the spring from direct contact with the cutting instrument and the second cutting instrument.

Any of the above aspects described herein can include any one or combination of the features disclosed herein.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

In describing the examples of the disclosure illustrated and to be described with respect to the drawings, specific terminology will be used for the sake of clarity. However, the disclosure is not intended to be limited to any specific terms or illustrations used herein, and it is to be understood that each specific term includes all technical equivalents.

The present disclosure is directed to an apparatus and methods that can be used in joint replacement that utilize a bone cutting instrument such as a reamer. The example description relates to a reamer used in a total or partial shoulder arthroplasty. However, the methods and apparatuses can be used for other joints. Thus, the concepts of the present application are not limited by the examples provided herein. The bone used herein is not limited to the scapula but can include any applicable bone of the body.

Figure 1A:
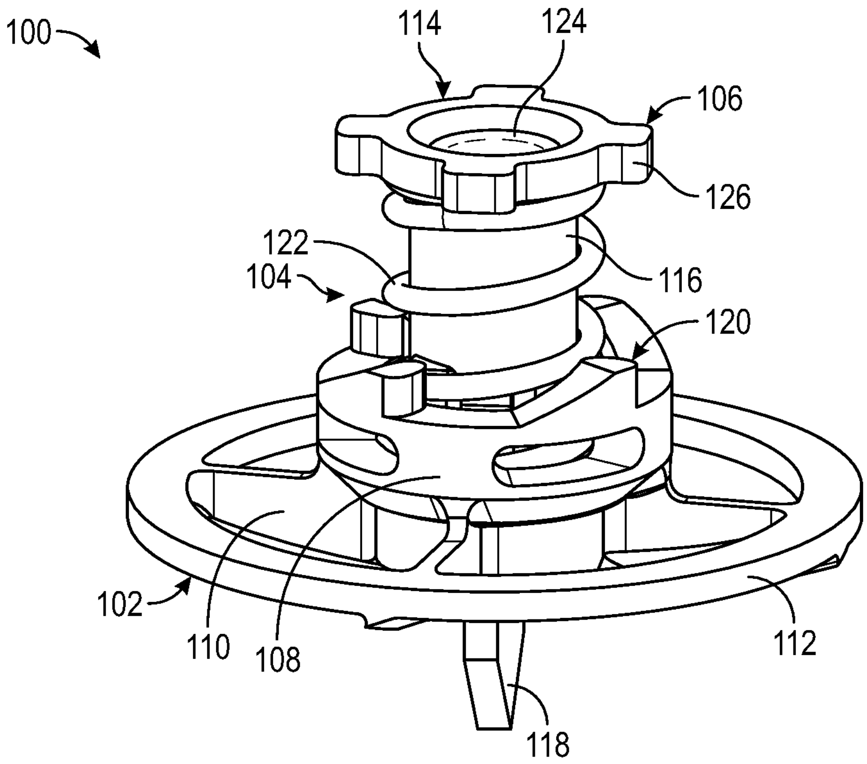
FIG. 1A is perspective view of a bone cutting instrument for a shoulder replacement procedure including a first component and a second component with the second component in a retracted position with respect to the first component according to an example of the present application.
Figure 1B:
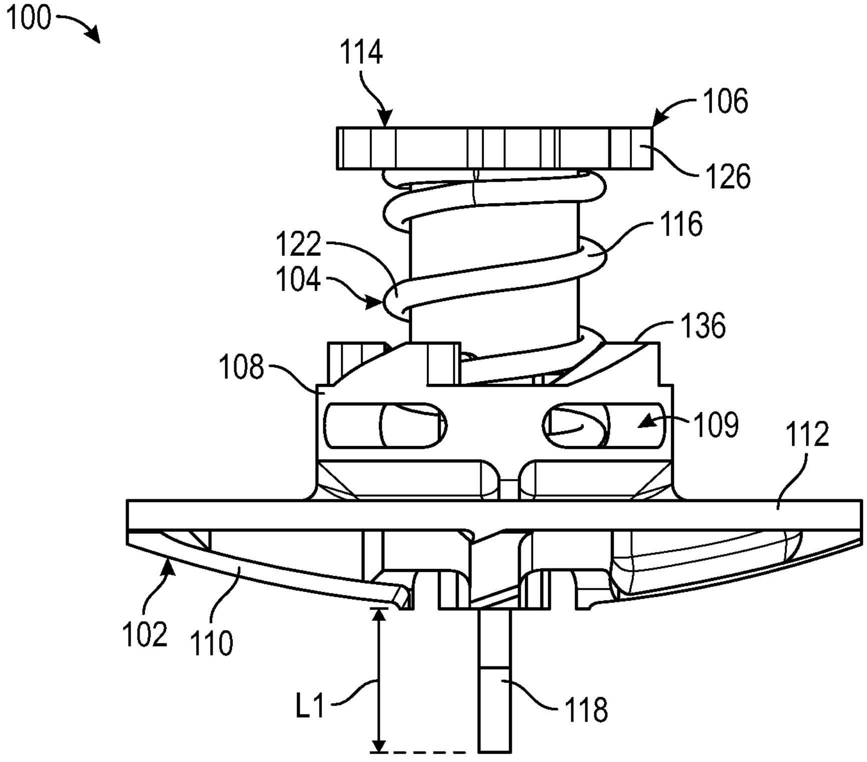
FIG. 1B is a plan view of a side the bone cutting instrument of FIG. 1A.

FIGS. 1A and 1B show a bone cutting instrument 100 including a first component 102, a retention assembly 104 and a second component 106. The first component 102 includes an inner body 108, cutting features 110, and outer web 112. The second component 106 includes a first one or more engagement features 114, a body 116 and cutting features 118.

The first component 102 can be a distinct first cutting instrument and the second component 106 can comprise a second distinct cutting instrument. The first component 102 can be coupled to the second component 106 by the retention assembly 104. The second component 106 can be moveable relative to the first component 102. The second component 106 can be telescopically or otherwise received by the first component 102. FIGS. 1A and 1B show the second component 106 in a retracted position or retracted state relative to the first component 102. This retracted position reduces a length L1 (FIG. 1B) the second component 106 protrudes distal of the first component 102.

The first component 102 can be a single piece integral component. The inner body 108 can be connected to the outer web 112 by the cutting features 110. The inner body 108 of the first component 102 can include a recess or thru hole 120 configured to receive the retention assembly 104 and the second component 106. The inner body 108 can be configured as a sleeve for the second component 106. As shown in FIG. 1B, the inner body 108 can include slots or other features 109 for accessing components of the retention assembly 104 and/or the second component 106 for cleaning. As also shown in FIG. 1B, the inner body 108 can include one or more engagement features 136 corresponding to and configured to be engaged by the one or more engagement features 114 such as one or more protrusions 126 when the second component 106 is moved into a deployed state or deployed position as further shown in FIGS. 3A-3C.

The cutting features 110 can extend radially or otherwise outward from the inner body 108. The cutting features 110 can include blades, teeth, tines, edges or other sharp features as known in the art. The cutting features 110 can be positioned to have bone cutting edges or other sharp features on a distal side of the first component 102. The cutting features 110 can configured (e.g., can be shaped, sized, positioned, etc.) to remove a fossa of a glenoid of a scapula, for example. Thus, the cutting features 110 can be generally curved or bowl shaped along the outer distal edge as shown in FIG. 1B.

The web 112 can comprise a ring that extends in circular or other shape around an outer circumference of the cutting features 110. The web 112 can be configured to allow smooth spinning of the bone cutting instrument 100 by stabilizing to avoid instability and shaking. The web 112 can also act as a visual depth stop in cases that are reaming depth is not controlled. The web 112 can structurally link the cutting features 110 together. Together the inner body 108, the cutting features 110 and the web 112 can form a hub, spoke and rim configuration for the first component 102 with openings allowing for the passage of cut bone.

The retention assembly 104 can include a spring 122 and additional components that will be discussed in further detail with regard to FIGS. 2 and 2A. The spring 122 can be configured to retain and bias the second component 106 to the retracted position or retracted state relative to the first component 102 as shown in FIGS. 1A and 1B. The spring 122 allows the bone cutting instrument 100 to return to the retracted position or retracted state of FIGS. 1A and 1B after use.

The one or more engagement features 114 can be parts of the body 116. The one or more engagement features 114 can be positioned at or adjacent a proximal side of the second component 106. The second component 106 can include a threaded aperture 124 or other mechanical feature(s) for coupling with a driver tool. Additionally, the one or more engagement features 114 can include one or more protrusions 126 for engagement with the first component 102 as further shown and discussed in FIG. 4. The one or more protrusions 126 can be arranged and can extend outward from a circumference of the body 116. The body 116 can be generally cylindrically or drum shaped so as to be moveably received by the first component 102 (via the recess or thru hole 120) and the retention assembly 104. A distal portion of the body 116 can connect with the cutting features 118. At least a portion of the cutting features 118 can be housed within the first component 102 when the second component 106 is in the retracted position or retracted state relative to the first component 102. Additionally, a distal portion of the cutting features 118 can extend distal of the first component 102 the length L1 shown in FIG. 1B. The cutting features 118 can be configured to remove at least a vault of the glenoid of the scapula, for example. The cutting features 118 can include blades, teeth, edges, point(s) or other sharp features as known in the art. The cutting features 118 can have a pointed tip geometry. However, other tip geometries (conical, frustoconical, semi-spherical, blunt, etc.) are contemplated. The cutting features 118 can be appropriately sized for insertion into the glenoid.

As discussed, the second component 106 can couple with a drive tool via the threaded aperture 124 or other features. The drive tool can comprise a reamer driver or other drive device as known in the art. Examples of such devices can be found in U.S. Pat. Nos. 10,687,831 and 10,945,862, the entire discloses of each of which are incorporated by reference in their entirety. The drive tool can include a shaft and a head, for example. The head can be configured as a thread, gear, hex or other type coupling device, for example. The drive tool can be configured to couple with and drive the bone cutting instrument 100. Rotation of the drive tool can initially be passed only to the second component 106 when the second component 106 is in the retracted position.

The bone cutting instrument 100 can be configured and used as a reamer. However, other types of bone cutting instruments designs such as broaches, drills, cannulated drills, needles, osteotomes, rongeurs, bone cutters, punches, etc. are also contemplated that could benefit from the construction of the first component and the second component as described herein.

Figure 1C:
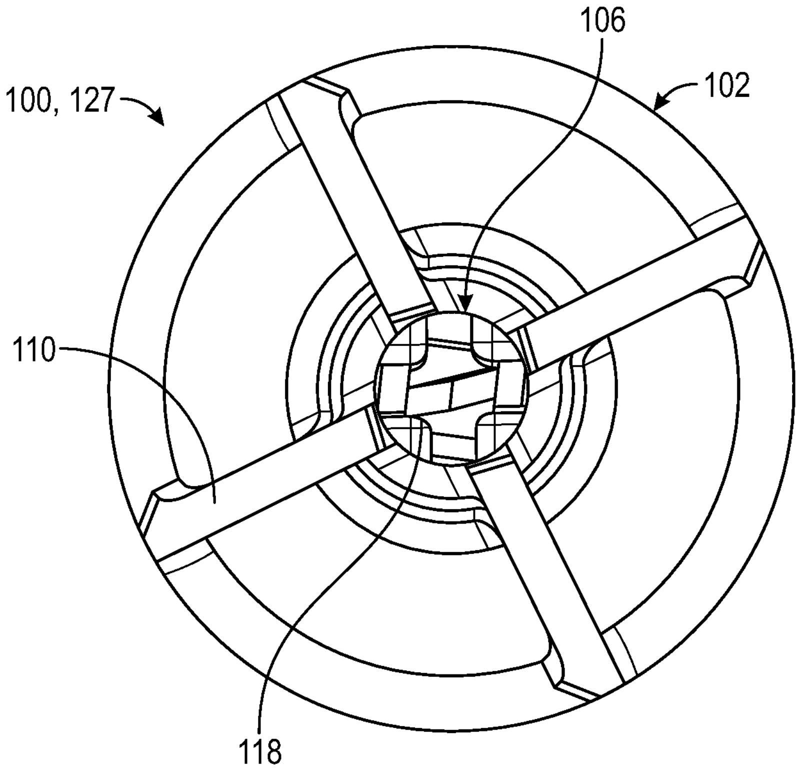
FIG. 1C is a plan view of a distal side of the bone cutting instrument of FIG. 1A.

FIG. 1C shows a distal side 127 of the bone cutting instrument 100, in particular, the cutting features 118 of the second component 106 and the cutting features 110 of the first component 102. As shown in FIG. 1C, when the second component 106 is in the retracted position or retracted state relative to the first component 102, the cutting features 118 of the second component 106 may not align with the cutting features 110 of the first component 102. As discussed, the second component 106 can be engaged by the drive tool and can be operated initially independently of the first component 102 to rotate, cut and remove the vault of the glenoid of the scapula before the second component 106 engages the first component 102 as shown in FIG. 4 for bone removal using both the first component 102 and the second component 106 for removing both the vault and the fossa of the glenoid. Thus, the first component 102 can initial be stationary while the second component 106 moves from the retracted position of FIGS. 1A-IC toward the position of FIGS. 3A-4.

Figure 1D:
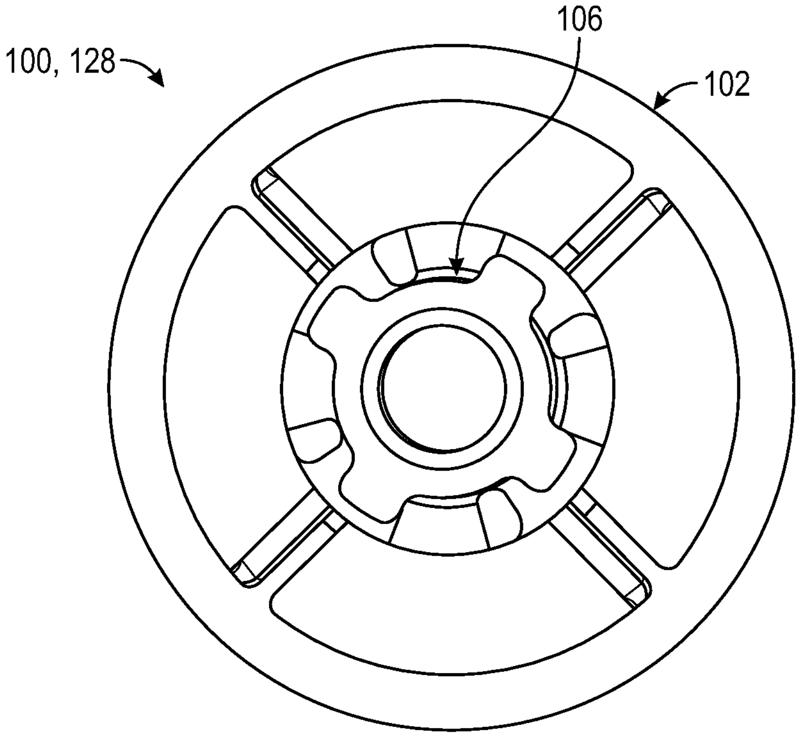
FIG. 1D is a plan view of a proximal side of the bone cutting instrument of FIG. 1A.

FIG. 1D shows an opposing proximal side 128 of the bone cutting instrument 100 with the second component 106 positioned within and proximal of the first component 102.

Figure 2:
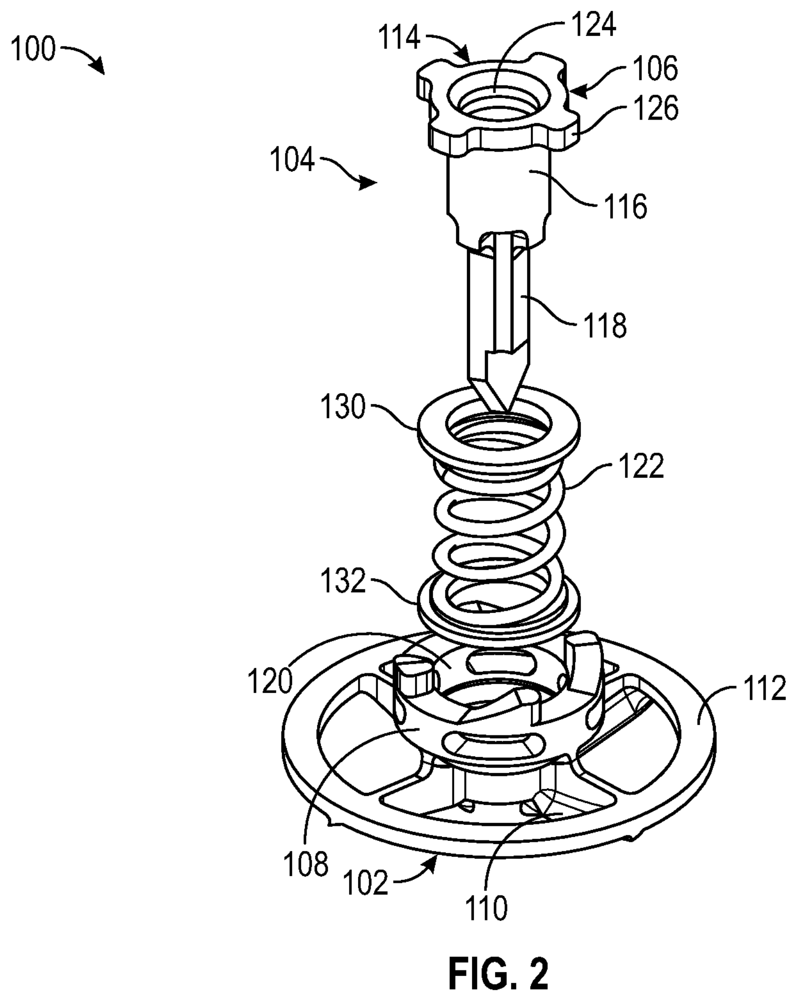
FIG. 2 is an exploded view of the bone cutting instrument of FIG. 1A showing a retention assembly in addition to the first component and the second component.

FIG. 2 shows an exploded view of the bone cutting instrument 100 with the first component 102, retention assembly 104 and the second component 106 disassembled and removed from coupling engagement with one another. The first component 102 can include the inner body 108, the cutting features 110, the web 112 and the thru hole 120, as discussed previously. The retention assembly 104 can include the spring 122 and additionally a first bushing 130 and a second bushing 132. The second component 106 includes the engagement features 114, the one or more protrusions 126, the body 116 including the threaded aperture 124, and the cutting features 118.

The first bushing 130 can be configured as a ring and can be fit or otherwise connected to the second component 106. The first bushing 130 can be engaged by a proximal end of the spring 122. The second bushing 132 can be configured as a ring and can be fit or otherwise connect to the first component 102. The second bushing 132 can be engaged by a distal end of the spring 122. The spring 122 can comprise a compression spring configured to bias the second component 106 toward and into the retracted position of FIGS. 1A-IC. The first bushing 130 and the second bushing 132 can be constructed of a different material than the first component 102 and the second component 106. Such material for the first bushing 130 and the second bushing 132 can be formed of a hard plastic (e.g., PEEK or the like), while the first component 102 and the second component 106 can be formed of a metal alloy, for example.

Figure 2A:
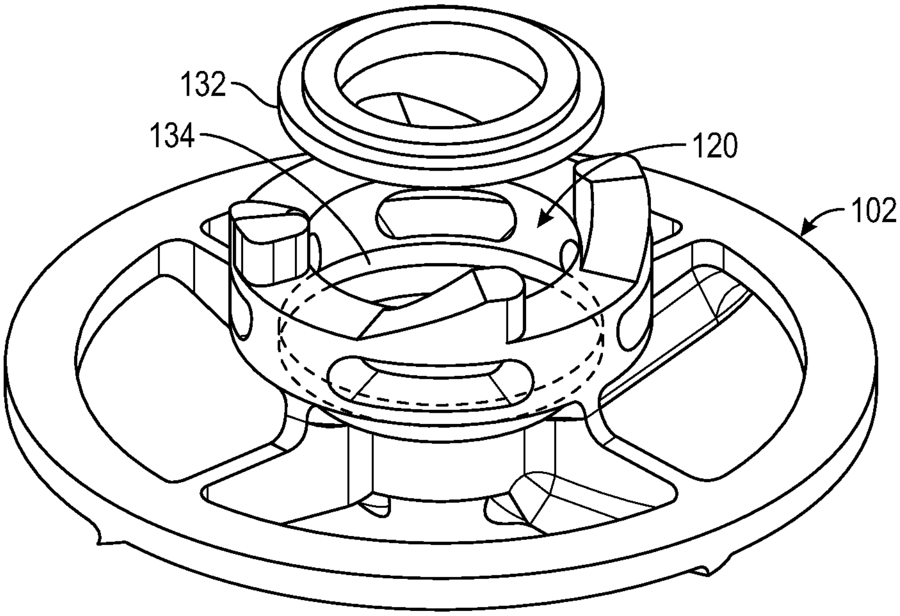
FIG. 2A is an enlarged view of a portion of the bone cutting instrument of FIG. 2.

FIG. 2A shows a groove 134 in the thru hole 120 that the second bushing 132 can be fit or otherwise inserted into. The first bushing 130 and the second bushing 132 provide bases for the spring 122 to engage with. The first bushing 130 and the second bushing 132 can insulate or otherwise separate the spring 122 from directly contacting the first component 102 and the second component 106.

Figure 3A:
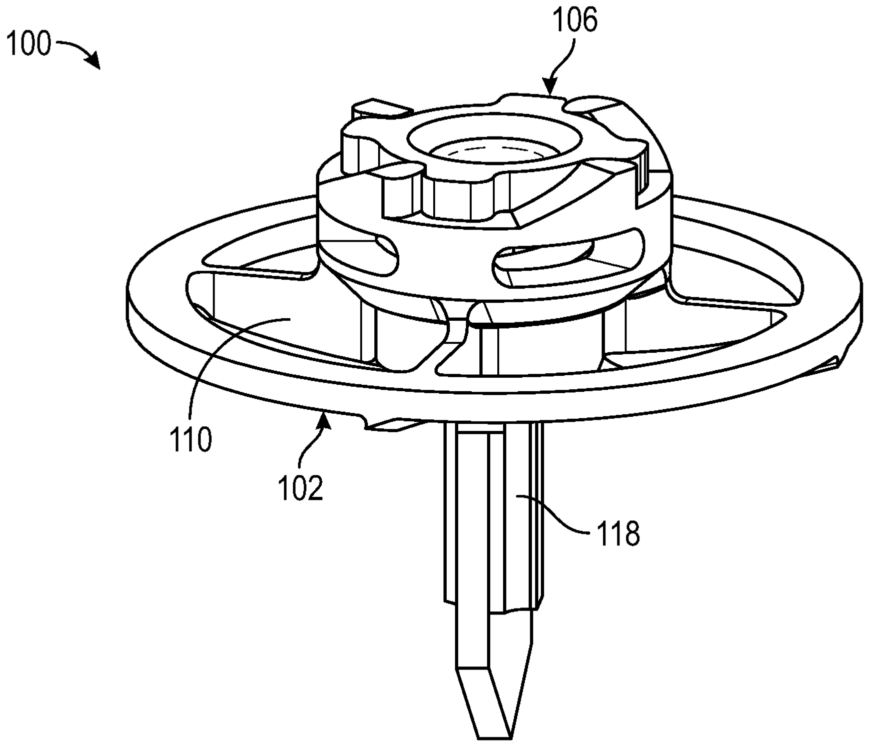
FIG. 3A is perspective view of the bone cutting instrument of FIG. 1A with the second component in a deployed position with respect to the first component according to an example of the present application.
Figure 3B:
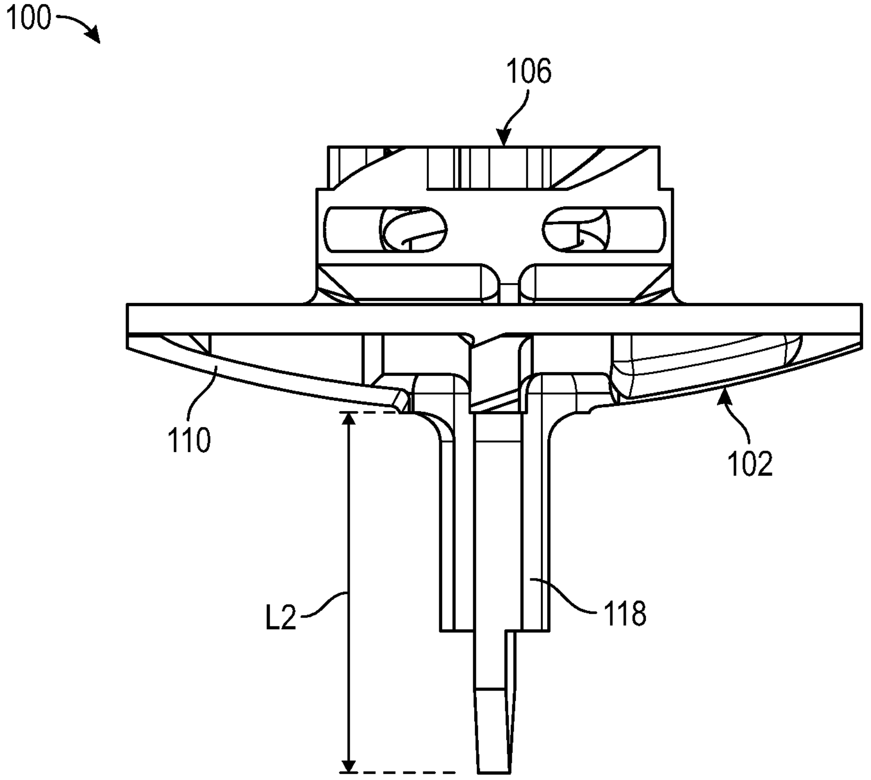
FIG. 3B is a plan view of a side of the bone cutting instrument of FIG. 3A.
Figure 3C:
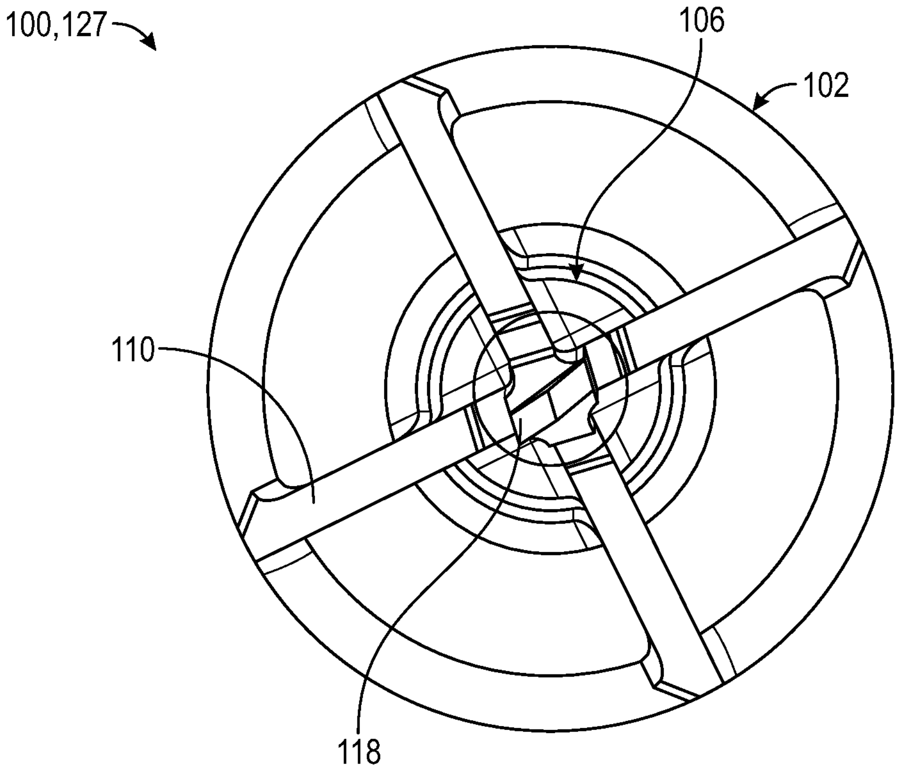
FIG. 3C is a plan view of the distal side of the bone cutting instrument of FIG. 3A.
Figure 4:
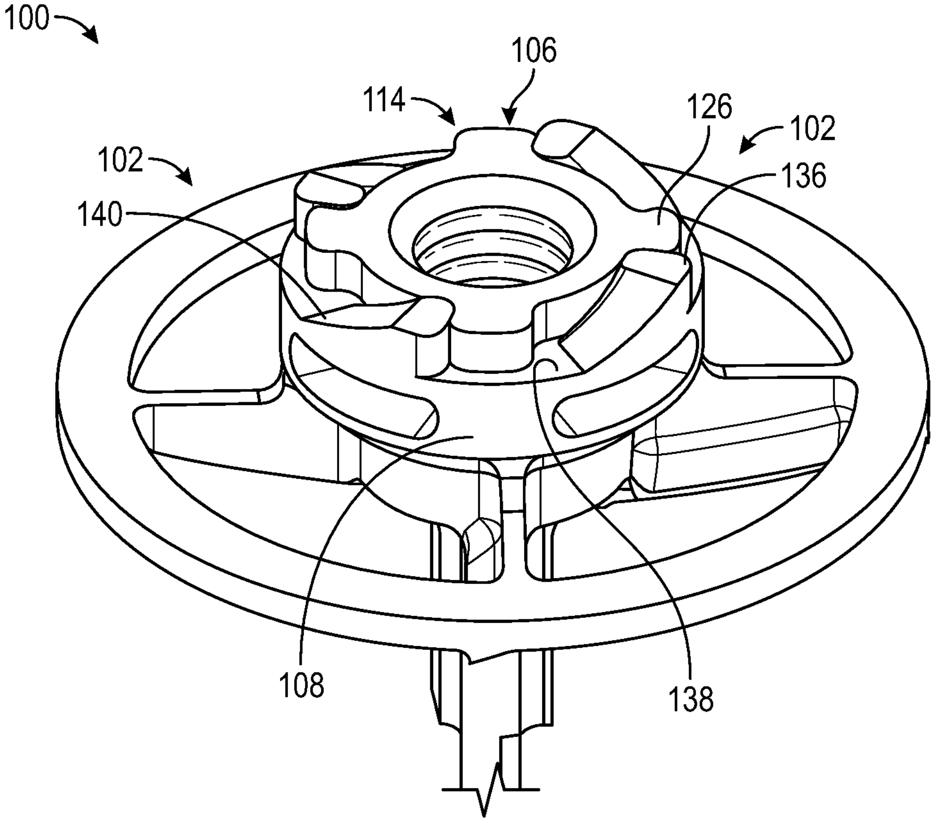
FIG. 4 is a perspective view showing engagement of protrusions of the second component engaging with corresponding engagement features of the first component for co-rotation of the first and second components according to an example of the present application.

FIGS. 3A-3C show the bone cutting instrument 100 with the second component 106 moved to a deployed state or deployed position relative to first component 102. This movement of the second component 106 compresses the spring 122 (FIG. 2). In the deployed state or deployed position, the second component 106 is moved distally down and engages the first component 102 for co-rotation and cutting of bone together using the cutting features 118 and the cutting features 110. The second component 106 is in a distally extended position with the cutting features 118 extending to a length L2 (FIG. 3B) past a distal-most end of the first component 102. The length L2 exceeds the length L1 of FIG. 1B.

FIG. 3C shows the distal side 127 of the bone cutting instrument 100, in particular, the cutting features 118 of the second component 106 and the cutting features 110 of the first component 102. As shown in FIG. 3C, when the second component 106 is in the deployed position or deployed state relative to the first component 102, the cutting features 118 of the second component 106 may substantially align with the cutting features 110 of the first component 102. This allows for a substantially continuous cutting of bone by the combined cutting features 110 and the cutting features 118. However, such alignment is not contemplated in all examples.

FIG. 4 shows a perspective view of the second component 106 in the deployed state or deployed position relative to first component 102. As shown in FIG. 4, the one or more engagement features 114, in particular the one or more protrusions 126, engage with corresponding engagement features 136 on a proximal surface 138 of the inner body 108 of the first component 102. Engagement between the one or more engagement features 114 and the corresponding engagement features 136 transfers torque and rotation from the second component 106 to the first component 102. This engagement of the one or more engagement features 114 with the corresponding engagement features 136 for co-rotation of the second component 106 with the first component 102 occurs when the second component 106 is moved down to the deployed state or deployed position relative to first component 102.

FIG. 4 additionally shows a plurality of ramps 140 positioned along the proximal surface 138 of the inner body 108 of the first component 102. The plurality of ramps 140 can be configured to guide and aid movement of the one or more engagement features 114, in particular the one or more protrusions 126, distally into engagement with the corresponding engagement features 136. The plurality of ramps 140 are optional and may not be included in some examples of the present application.

As discussed previously, the retraction of the second component 106 proximally reduces the initial distal length (L1 of FIG. 1B) of the bone cutting instrument 100. This reduced distal length for the second or vault cutting component allows the bone cutting instrument 100 to have a easier access upon approach to the glenoid allowing for easier positioning of the bone cutting instrument 100 relative to the glenoid by the surgeon.

According one example, a method of cutting a bone during an orthopedic surgical procedure is disclosed. The method can include rotating and inserting at least a portion of a cutting instrument through a second cutting instrument to remove at least part of a vault of the scapula. The method can include engaging the cutting instrument with the second cutting instrument. Upon the engaging, the method can include rotating the cutting instrument and the second cutting instrument to remove a fossa of the scapula and a remaining part of a vault of the scapula. A plurality of engagement protrusions can be used for engaging the second cutting instrument. The method can include passing at least some of the plurality of engagement protrusions along ramps of the second cutting instrument. The cutting features of the cutting instrument and the second cutting instrument can be aligned upon the engaging of the cutting instrument with the second cutting instrument. Rotating and inserting the at least the portion of the cutting instrument can include compressing a spring coupled between the cutting instrument and the second cutting instrument. The method can include isolating the spring from direct contact with the cutting instrument and the second cutting instrument.

The term "proximal" refers to the general orientation of the side and/or surface when the cutting instrument is utilized to cut tissue. Thus, "proximal" refers to a direction or location generally in the direction of or toward a driver, and "distal" refers to the opposite direction of proximal, i.e., away from the driver. As used herein, the terms "anterior" and "posterior" should be given their generally understood anatomical interpretation. Thus, "posterior" refers to a location or direction generally toward a rear of the patient. Similarly, "anterior" refers to a location or direction generally toward a front of the patient. Thus, "posterior" refers to the opposite direction of "anterior." Similarly, the terms "medial" and "lateral" should be given their generally understood anatomical interpretation. "Medial" refers to the more inward facing (inner part) of the guide or instrument (when in the implanted orientation) and "lateral" refers to the outer part or outward facing part. "Medial" refers to the opposite direction of "lateral."

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims. For example, the order of method steps or stages can be altered from that described above, as would be appreciated by a person of skill in the art.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An apparatus for removing part of a scapula during an orthopedic shoulder procedure, comprising:

a first component having one or more cutting features configured to remove a fossa of a scapula;

a second component having one or more cutting features configured to remove at least a vault of the scapula, wherein the second component is selectively moveable relative to the first component between a retracted position and a deployed position, wherein the second component and the first component are coupled together for rotation when the second component is in the deployed position;

a first plurality of engagement features positioned along the first component;

a second plurality of engagement features positioned along the second component, wherein rotation of the second component brings the second plurality of engagement features into contact with the first plurality of engagement features to engage the second component with the first component for removing the fossa and the vault simultaneously;

one or more ramps that pass the second plurality of engagement features to the first plurality of engagement features; and a retention assembly configured to couple the first component with the second component, the retention assembly including:

a first bushing coupled to the first component;

a second bushing coupled to the second component; and a spring engaging the first bushing and the second bushing, wherein the spring is configured to bias the second component to the retracted position relative to the first component.

2. The apparatus of claim 1, wherein the one or more cutting features of the second component substantially align with the one or more cutting features of the first component when the second component is in the deployed position and engaged with the first component for removing the scapula.

3. A method of cutting a bone during an orthopedic surgical procedure, the method comprising:

rotating and inserting at least a portion of a first cutting instrument through a second cutting instrument to remove at least part of a vault of a scapula, wherein the first cutting instrument has one or more cutting features to remove the at least part of the vault of the scapula, wherein the first cutting instrument is selectively moveable relative to the second cutting instrument between a retracted position and a deployed position, wherein the second cutting instrument has one or more cutting features configured to remove a fossa of the scapula; and engaging the first cutting instrument with the second cutting instrument with a retention assembly configured to couple the second cutting instrument with the first cutting instrument but allow the first cutting instrument to be selectively moveable relative to the second cutting instrument while the first cutting instrument is in the retracted position relative to the second cutting instrument, the retention assembly including:

a first bushing coupled to the second cutting instrument;

a second bushing coupled to the first cutting instrument; and a spring engaging the first bushing and the second bushing, wherein the spring biases the first cutting instrument to the retracted position relative to the second cutting instrument;

bringing, via rotation of the first cutting instrument, a first plurality of engagement features positioned along the first cutting instrument into contact with a second plurality of engagement features positioned along the second cutting instrument via one or more ramps that pass the first plurality of engagement features to the second plurality of engagement features, thereby coupling the first cutting instrument and the second cutting instrument together for rotation when the first cutting instrument is in the deployed position; and upon the engaging, rotating the first cutting instrument and the second cutting instrument to remove the fossa of the scapula and the vault of the scapula simultaneously.

4. The method of claim 3, wherein the engaging the first cutting instrument with the second cutting instrument is via a plurality of engagement protrusions.

5. The method of claim 4, further comprising passing at least some of the plurality of engagement protrusions along one or more ramps.

6. The method of claim 3, wherein a cutting feature of the first cutting instrument and a cutting feature of the second cutting instrument are aligned upon the engaging of the first cutting instrument with the second cutting instrument.

7. The method of claim 3, wherein rotating the first cutting instrument and the second cutting instrument includes inserting and compressing the spring.

8. The method of claim 7, further comprising isolating the spring from direct contact with the first cutting instrument and the second cutting instrument via the first bushing and the second bushing.

* * * * *